US00PP31105P2

(12) United States Plant Patent
Olesen

(10) Patent No.: US PP31,105 P2
(45) Date of Patent: Nov. 26, 2019

(54) MINIATURE ROSE PLANT NAMED 'POULPAR091'

(50) Latin Name: ***Rosa* hybrid**
Varietal Denomination: Poulpar091

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,582

(22) Filed: Sep. 4, 2018

(51) Int. Cl.
*A01H 5/02* (2018.01)
*A01H 6/74* (2018.01)

(52) U.S. Cl.
USPC ..... Plt./120
CPC ..... *A01H 6/74* (2018.05); *A01H 5/02* (2013.01)

(58) Field of Classification Search
USPC ..... Plt./116, 119, 120, 123, 126, 127
CPC ..... A01H 5/0222
See application file for complete search history.

(56) References Cited

PUBLICATIONS http://www.helpmefind.com/rose/l.php?I=2.71232.0; No Date; 1 page.*

* cited by examiner

*Primary Examiner* — Kent L Bell

(57) ABSTRACT

A new garden rose plant of the miniature class which has abundant, peach blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar091'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpar091', originated as a single seedling from the stated cross.

The new variety may be distinguished from its male pollen parent and female seed parent primarily by the following characteristics. The male pollen parent plant has a growth height of 25 to 30 cm, while the new variety has a growth height of 35 cm. The female seed parent plant has yellow flowers while the new variety has peach blend flowers.

The objective of the hybridization of this rose variety was to create a new and distinct variety with unique qualities, such as:

1. Uniform and abundant peach blend flowers;
2. Vigorous, but compact growth when propagated on its own roots;
3. Exceptional disease resistance.

This combination of qualities is not present in previously available commercial cultivars of this type, known to the inventor, and distinguish 'Poulpar091' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar091' was selected in the spring of 2008 by the inventor as a single plant from the progeny of the aforementioned hybridization.

Asexual reproduction of 'Poulpar091' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpar091' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar091'.

Specifically illustrated in FIG. 1 of the drawings are an open flower, petals detached, flower buds, sepals detached, and reproductive flower parts.

Figure 1:
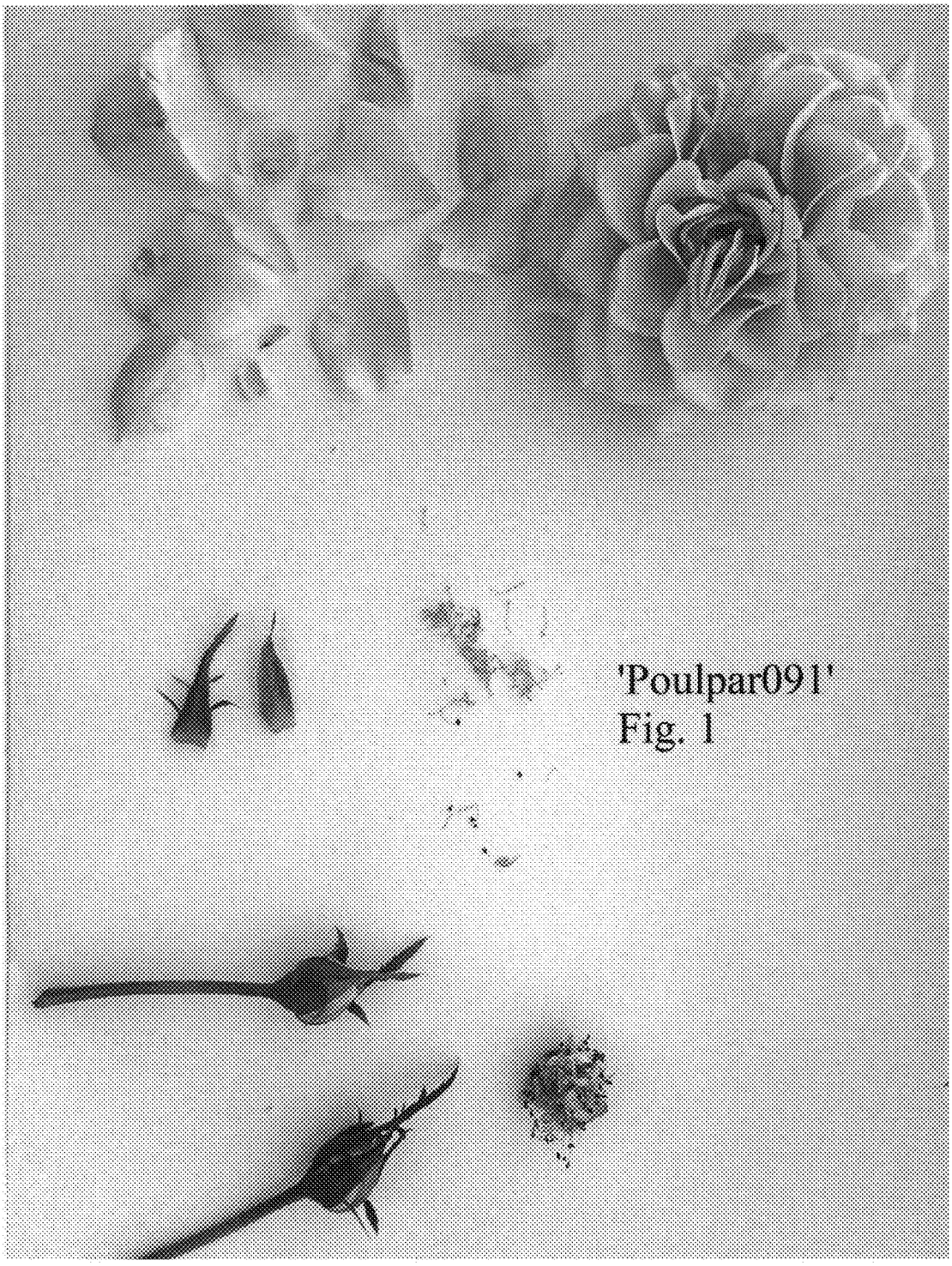
Figure 2:
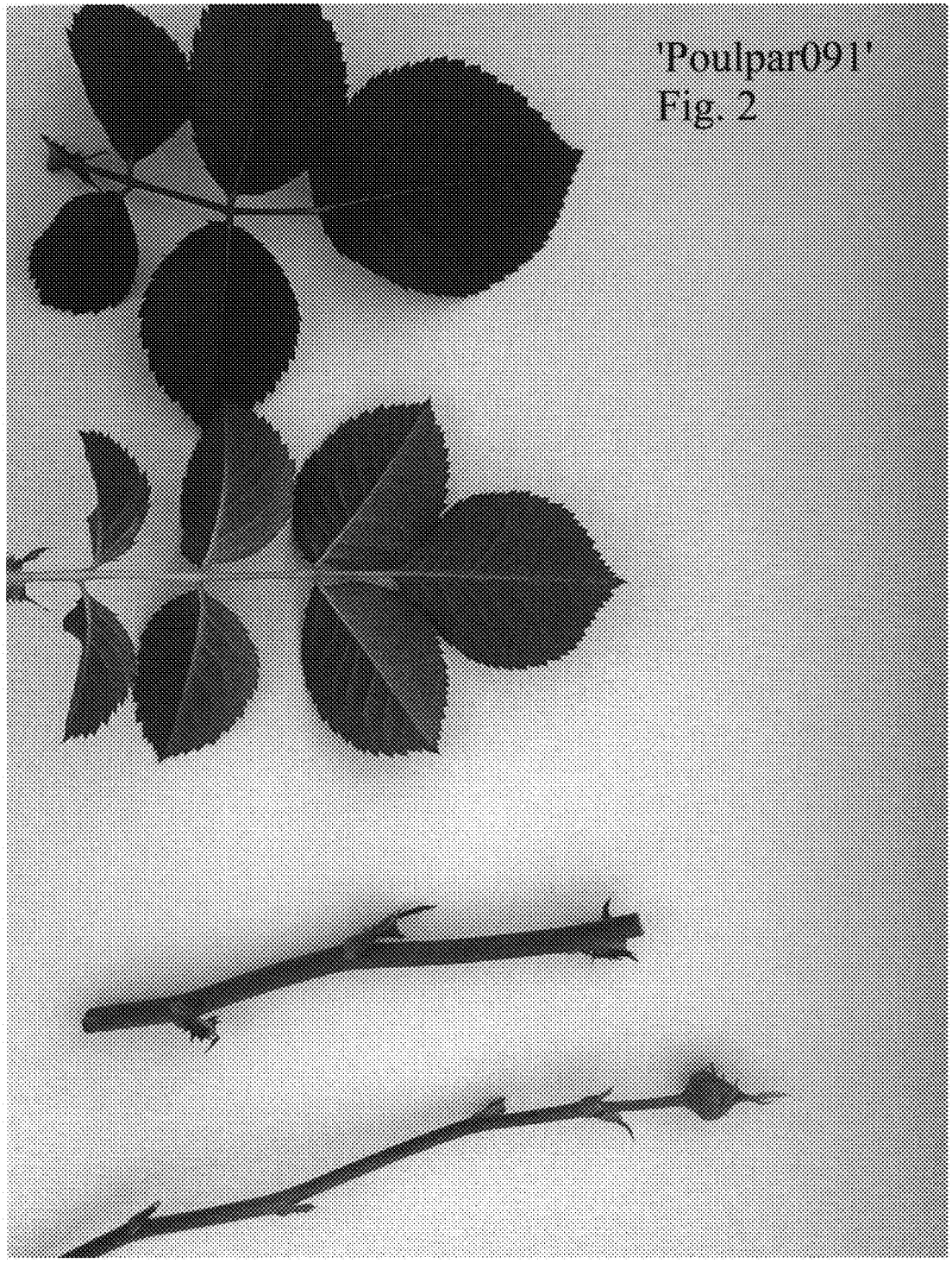

Specifically illustrated in FIG. 2 of the drawings are leaves and bare stems. Plants shown are 2 years of age.

DETAILED DESCRIPTION OF THE VARIETY

The following is a description of 'Poulpar091', as observed in its growth in a container nursery in Denmark. Observed plants are 12 months age, and were grown on their own roots in 24 cm pots. Color references are made using The Royal Horticultural Society (London, England) Colour Chart, 2001, except where common terms of color are used.

For a comparison, several physical characteristics of the rose variety 'Poulpar090', U.S. Plant Pat. No. 28,044 are compared to 'Poulpar091' in Chart 1.

CHART 1

Comparison with 'Poulpar090'

| | 'Poulpar091' | 'Poulpar090' |
|---|---|---|
| Petal Count | 100 | 80 |
| Flower Diameter | 60 to 75 mm | 70 mm |
| General Tonality of Flower Color | Yellow-Orange Group 20B | Yellow-Orange Group 20D |

Flower and Flower Bud

Blooming habit: Continuous.

Flower bud:

*Size.*—Upon opening, 30 mm in length from base of receptacle to end of bud. Bud diameter is 11 mm.

*Bud form.*—Urceolate.

*Bud color.*—As sepals divide petals are Yellow Group 13C.

*Sepal inner surface.*—Color: Green Group 138C. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—18 to 30 mm long, 5 to 7 mm wide.

*Receptacle.*—Texture: Smooth. Size: 4 mm in height, 7 mm wide. Color: Yellow-Green Group 144A. Shape: Funnel.

*Pedicel.*—Surface: Smooth. Length: 40 to 50 mm. Diameter: 2.5 mm on average. Color: Yellow-Green Group 144A. Strength: Moderate.

*Peduncle.*—Length: 3 to 5 cm. Diameter: About 3.5 mm. Color: Yellow-Green Group 146A. Texture: Smooth.

Flower bud development: Flower buds are borne singly, and in clusters of 3 to 8 flower buds per stem. Development as a Corymb.

Flower bloom:

*Fragrance.*—Moderate.

*Duration.*—The blooms have a duration on the plant of approximately 20 days. Petals fall cleanly away from plant after flowers have fully matured.

*Size.*—Flower diameter is 60 to 75 mm when open. Flower depth is 30 mm.

*Flower shape.*—Rosette very double flower with many slightly overlapping petals of different sizes.

*Shape of flower, side view.*—The upper portion is flat. The lower portion is concave.

Petalage: Under normal conditions, flowers have about 100 petals.

General tonality of flower: Open flowers are Yellow-Orange Group 20B.

Petal color:

*Upon and after opening, outer petals.*—Upper surface: Yellow-Orange Group 20C. Lower surface: Yellow-Orange Group 20C with light intonations of Orange Group 29B.

*Upon and after opening, inner petals.*—Upper surface: Yellow-Orange Group 20C. Lower surface: Yellow-Orange Group 20C shaded with light intonations of Orange Group 29B.

*Basal petal spots, upon and after opening.*—Upper surface: Yellow Group 10D. Lower surface: Yellow Group 10D.

Petals:

*Petal reflex.*—Outer petals exhibit strong reflex. Inner petals do not reflex.

*Margin.*—Entire and uniform. Moderate undulations.

*Shape.*—Narrow elliptic, and ovate. Apex shape: Rounded with a slight point. Base shape: Acute.

*Size.*—35 mm (l)×35 mm (w).

*Texture.*—Smooth.

*Thickness.*—Average.

Petaloids:

*Size.*—20 mm (l) by 15 mm (w).

*Quantity.*—About 40.

*Shape.*—Irregular, and elliptical with an acute base and rounded apices.

*Color.*—The upper surface is Yellow-Orange Group 20C. The lower surface is Yellow-Orange Group 20C shaded with light intonations of Orange Group 29B. Small spots at the base of the petaloid are Yellow Group 10D on the upper and lower surface.

Reproductive flower parts:

*Pollen.*—None observed.

*Anthers.*13 Size: 1 mm in length. Color: Greyed-Orange Group 166A. Quantity: 45 on average.

*Filaments.*—Color: Yellow-Orange Group 16B. Length: 4 mm.

*Pistils.*—Length: 8 mm. Quantity: 40 to 50.

*Stigmas.*—Color: Yellow Group 12B.

*Styles.*—Color: Green-Yellow Group 1C.

*Location of stigmas.*—Superior in location relative to the length of the filaments and the height of the anthers.

*Hips.*—None Observed.

Plant

Plant growth: Upright, bushy. Plants are 35 cm in height, and 35 cm wide.

Stems:

*Color of juvenile growth.*—Yellow-Green Group 144B.

*Color of mature growth.*—Yellow-Green Group 146A.

*Length.*—Canes are about 30 cm from the base of the plant to the flowering portion.

*Diameter.*—About 5 mm.

*Internodes.*—On mature canes about 3 mm between nodes.

*Surface texture.*—Young wood: Smooth. Older wood: Smooth.

Long prickles:

*Incidence.*—0 to 4 prickles per 10 cm of stem, mainly at the base of the plant.

*Size.*—Average length of prickles on mature stems is 5 mm.

*Shape.*—Upper portion is linear. Lower portion is concave.

*Color*.—Juvenile prickles: Greyed-Orange Group 167C. Mature prickles: Greyed-Orange Group 167C.

Plant foliage:

*Compound leaf*.—80 to 100 mm (l)×50 to 100 mm (w).

*Quantity*.—3 leaves per 10 cm of stem on average.

*Leaf bearing angle to the stem*.—45 degrees.

*Color of juvenile foliage*.—Upper side: Yellow-Green Group 146A. Lower side: Yellow-Green Group 147C.

*Color of mature foliage*.—Upper side: Yellow-Green Group 147A. Lower side: Yellow-Green Group 147C.

Plant leaves and leaflets:

*Stipules*.—Size: 10 mm long, 3 mm wide. Quantity: 2 per compound leaf. Shape: Linear, slightly broad based with outward extending apices. Margins: Finely serrated. Color: Yellow-Green Group 147B.

*Petiole*.—Length: 5 to 10 mm. Diameter: 1.5 mm. Upper surface color: Yellow-Green Group 147B. Lower surface color: Yellow-Green Group 146B.

*Rachis*.—Length: 10 to 20 mm. Diameter: About 2 mm. Upper surface color: Yellow-Green Group 147B. Lower surface color: Yellow-Green Group 146B.

*Leaflet*.—Quantity: Normally 5 to 7 leaflets. Margins: Serrated. Size: Terminal leaflets are 35-55 mm long, and 30 to 45 mm wide. Shape: Generally ovate. Base: Rounded. Apex: Acute. Texture: Smooth. Thickness: Average. Arrangement: Odd pinnate. Venation: Reticulate. Glossiness: None.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant named 'Poulpar091', substantially as illustrated and described herein, due to its abundant peach blend flowers, disease resistance, and extended period of bloom.

* * * * *

'Poulpar091'

'Poulpar091'